(12) United States Patent
Konno

(10) Patent No.: US 10,883,186 B2
(45) Date of Patent: Jan. 5, 2021

(54) PLATING PROCESSING METHOD OF GRIPPING SURFACE OF GRIPPING TOOL, AND GRIPPING TOOL

(71) Applicant: Just Co., Ltd., Yamagata (JP)

(72) Inventor: Takashi Konno, Kaminoyama (JP)

(73) Assignee: Just Co., Ltd., Yamagata (CN)

( * ) Notice: Subject to any disclaimer, the term of this patent is extended or adjusted under 35 U.S.C. 154(b) by 360 days.

(21) Appl. No.: 15/905,939

(22) Filed: Feb. 27, 2018

(65) Prior Publication Data

US 2018/0187325 A1 Jul. 5, 2018

Related U.S. Application Data

(62) Division of application No. 14/996,779, filed on Jan. 15, 2016, now Pat. No. 9,957,633.

(30) Foreign Application Priority Data

Jun. 29, 2015 (JP) .................. 2015-129365

(51) Int. Cl.
   *B32B 15/04* (2006.01)
   *C25D 15/00* (2006.01)
   (Continued)

(52) U.S. Cl.
   CPC ............ *C25D 15/00* (2013.01); *A61B 17/062* (2013.01); *A61B 17/30* (2013.01);
   (Continued)

(58) Field of Classification Search
   None
   See application file for complete search history.

(56) References Cited

U.S. PATENT DOCUMENTS 3,488,892 A   1/1970   Benner
4,302,300 A   11/1981  Chamska et al.
(Continued)

FOREIGN PATENT DOCUMENTS

AT   368053 B    9/1982
EP   0004449 B1  12/1981
(Continued)

OTHER PUBLICATIONS

"U.S. Appl. No. 14/996,779, Advisory Action dated Nov. 6, 2017", 3 pgs.

(Continued)

*Primary Examiner* — Seth Dumbris
(74) *Attorney, Agent, or Firm* — Schwegman Lundberg & Woessner, P.A.

(57) ABSTRACT

A plating processing method of a gripping surface of a gripping tool includes: temporarily and evenly fixing a plurality of first diamond grains having a uniform first grain diameter; adhering the first diamond grains by depositing a metal containing nickel on a gripping surface in a uniform thickness after the first diamond grains have been temporarily fixed; placing a plurality of second diamond grains having a second grain diameter on a metal surface of the gripping surface on which first diamond grains are not present; and adhering the second diamond grains by further depositing a metal containing nickel within a second plating solution on the metal surface in a uniform thickness that does not exceed the first diameter grain and the second diameter grain until a position relationship between the metal surface and the second diamond grains is not displaced even when the gripping tool is moved.

4 Claims, 16 Drawing Sheets

(51) Int. Cl.
    *C25D 5/14*     (2006.01)
    *C25D 7/00*     (2006.01)
    *C23C 28/02*     (2006.01)
    *C23C 18/16*     (2006.01)
    *C23C 18/32*     (2006.01)
    *C25D 5/02*     (2006.01)
    *A61B 17/30*     (2006.01)
    *A61B 17/062*     (2006.01)
    *A61B 17/28*     (2006.01)
    *A61B 17/00*     (2006.01)

(52) U.S. Cl.
    CPC ...... *C23C 18/1605* (2013.01); *C23C 18/1653* (2013.01); *C23C 18/1662* (2013.01); *C23C 18/32* (2013.01); *C23C 28/021* (2013.01); *C23C 28/023* (2013.01); *C23C 28/027* (2013.01); *C25D 5/022* (2013.01); *C25D 5/14* (2013.01); *C25D 7/00* (2013.01); *A61B 17/28* (2013.01); *A61B 2017/00429* (2013.01); *A61B 2017/00526* (2013.01); *A61B 2017/00858* (2013.01); *A61B 2017/305* (2013.01); *Y10T 428/12056* (2015.01)

(56) References Cited

U.S. PATENT DOCUMENTS

| | | | |
|---|---|---|---|
| 5,036,733 A * | 8/1991 | Tiholiz | A61B 17/2812 76/119 |
| 5,049,165 A * | 9/1991 | Tselesin | B24D 3/06 51/295 |
| 5,639,284 A | 6/1997 | Ryoke et al. | |
| 5,798,033 A | 8/1998 | Uemiya et al. | |
| 5,921,856 A | 7/1999 | Zimmer | |
| 6,022,348 A * | 2/2000 | Spitzer | A61B 17/6466 606/324 |
| 6,306,025 B1 * | 10/2001 | Torii | B24B 53/12 451/443 |
| 6,347,905 B1 * | 2/2002 | Lukschandel | F16B 2/005 403/404 |
| 2016/0376721 A1 | 12/2016 | Konno | |

FOREIGN PATENT DOCUMENTS

| | | |
|---|---|---|
| JP | S6034812 U | 3/1985 |
| JP | 63022275 A | 1/1988 |
| JP | H11000868 A | 1/1999 |
| JP | 2006239279 | 9/2006 |
| JP | 2012090724 | 5/2012 |

OTHER PUBLICATIONS

"U.S. Appl. No. 14/996,779, Examiner Interview Summary dated Nov. 29, 2017", 2 pgs.

"U.S. Appl. No. 14/996,779, Final Office Action dated Aug. 17, 2017", 7 pgs.

"U.S. Appl. No. 14/996,779, Non Final Office Action dated Apr. 18, 2017", 8 pgs.

"U.S. Appl. No. 14/996,779, Notice of Allowance dated Dec. 12, 2017", 7 pgs.

"U.S. Appl. No. 14/996,779, Response filed Mar. 27, 2017 to Restriction Requirement dated Jan. 25, 2017", 6 pgs.

"U.S. Appl. No. 14/996,779, Response filed Jul. 17, 2017 to Non Final Office Action dated Apr. 18, 2017", 6 pgs.

"U.S. Appl. No. 14/996,779, Response filed Oct. 17, 2017 to Final Office Action dated Aug. 17, 2017", 6 pgs.

"U.S. Appl. No. 14/996,779, Response filed Nov. 17, 2017 to Advisory Action dated Nov. 6, 2017", 6 pgs.

"U.S. Appl. No. 14/996,779, Restriction Requirement dated Jan. 25, 2017", 6 pgs.

"German Application Serial No. 102016101132.0, Office Action dated Feb. 26, 2016", w/English Translation, 16 pgs.

"Japanese Application Serial No. 2015-129365, Decision to Grant dated Sep. 24, 2015", w/English Translation, 6 pgs.

"Japanese Application Serial No. 2015-129365, Notice of Rejection Ground dated Jul. 28, 2015", w/ English Translation, 16 pgs.

Enomoto, Hidehiko, et al., "Composite Plating", w/ partial English translaiton, (1989), 10 pgs.

Tomono, Rihei, "Practical Manual for Plating", w/ partial English Translation, (Oct. 25, 1971), 6 pgs.

* cited by examiner

| | AREA OF GRIPPING PART = CIRCLE OF φ1.5 | | |
|---|---|---|---|
| | 50 μm | 30 μm | NOT PROCESSED |
| MAXIMUM | 5.9 | 6.6 | 60.9 |
| AVERAGE | 3.7 | 5.0 | 57.9 |
| MINIMUM | 1.0 | 3.0 | 53.9 |

| STAINLESS FOIL | | | |
|---|---|---|---|
| φ1.5 | 50 μm | 30 μm | NOT PROCESSED |
| MAXIMUM | 59.20 | 62.20 | 193.50 |
| AVERAGE | 57.13 | 59.90 | 190.33 |
| MINIMUM | 53.50 | 56.70 | 187.40 |

| PAPER | | | |
|---|---|---|---|
| φ1.5 | 50 μm | 30 μm | NOT PROCESSED |
| MAXIMUM | 46.40 | 47.05 | 135.50 |
| AVERAGE | 44.13 | 45.50 | 135.35 |
| MINIMUM | 42.60 | 44.60 | 135.20 |

FIG. 6C

| CHICKEN SKIN | | | |
|---|---|---|---|
| φ1.5 | 50 μm | 30 μm | NOT PROCESSED |
| MAXIMUM | 24 | 50 | 178 |
| AVERAGE | 19 | 38 | 164 |
| MINIMUM | 15 | 27 | 153 |

PLATING PROCESSING METHOD OF GRIPPING SURFACE OF GRIPPING TOOL, AND GRIPPING TOOL

CLAIM FOR PRIORITY

This application is a divisional of and claims the benefit of priority to U.S. application Ser. No. 14/996,779, filed Jan. 15, 2016, which claims priority to the Japanese Patent Application No. 2015-129365, filed on Jun. 29, 2015, entitled "PLATING PROCESSING METHOD OF GRIPPING SURFACE OF GRIPPING TOOL, AND GRIPPING TOOL" which are incorporated herein by reference in their entireties.

BACKGROUND OF THE INVENTION

Field of the Invention

The present invention relates to a plating processing method of a gripping surface of a gripping tool, and a gripping tool.

Description of the Related Art

Gripping tools used in surgical operations for neurosurgery, cardiac surgery or the like include a needle holder, which is a tool for gripping a sewing needle, micro-tweezers (forceps) used in an operation, and the like. In particular, a preferable technique for further improving a gripping force is needed for medical gripping tools used in operations (microsurgery) that have a premium placed on delicate movements and sensation in the fingertips under a lens, especially a microscope, an endoscope or the like.

For a needle holder, a gripping surface (chip) suitable for the size of a sewing needle used in accordance with the type of an operation is employed. As illustrated in FIG. 10, there are needle holder gripping surfaces suitable for sewing needle sizes from 5 to 0, and from 0-2 to 0-12. For some needle holders, the gripping surface of the needle holder suitable for a sewing needle larger than the size 0-10 is structured so that protrusions in a square pyramid shape are brazed onto the gripping surface, and the square pyramids are engaged with one another (see #2500 to #16000 in FIG. 10). The number after #in FIG. 10 represents the number of vertical and horizontal lines per square inch. For example, #16000 indicates that the number of vertical and horizontal lines is 1600 per square inch, and that the length of one of the bottom sides of the square pyramid is approximately 1.6 µm in this case.

As a related technique, for example, Japanese Laid-open Patent Publication No. 2012-90724 proposes a microsurgical instrument which can reduce the burden on the fingertips, and especially the burden on the thumb, and in which one arm is provided with an attachable and detachable support member so that sensation and movement of the fingertips, and especially the sensation of the thumb can be concentrated on opening and closing movements at a tip.

Additionally, for example, Japanese Laid-open Patent Publication No. 2006-239279 proposes medical tweezers in which a gripping part at a tip of the tweezers grips a living tissue with a suitable force by being provided with opening and closing means that are opened and closed via an elastic member, and with which a surgical operation can be performed easily without damaging the living tissue.

SUMMARY OF THE INVENTION

A plating processing method of a gripping surface of a gripping tool according to a first aspect of the present invention includes: placing the gripping tool in a bottom of a first plating solution, which is an electroplating solution containing nickel ion as a main ingredient, so that the gripping surface can become horizontal; placing, on the gripping surface, a plurality of first diamond grains having a uniform grain diameter in a quantity that can cover the gripping surface, and temporarily fixing the first diamond grains onto the gripping surface by depositing nickel on the gripping surface in a state where the gripping surface is made stationary until a position relationship between the gripping surface and the first diamond grains is not displaced even when the gripping tool is moved; removing first diamond grains that are not temporarily fixed after the first diamond grains have been temporarily fixed; placing, in a bottom of the electroplating solution containing nickel ion as a main ingredient or in a second plating solution that is an electroless plating solution that forms a nickel alloy film with autocatalysis, the gripping tool in a manner such that the gripping surface becomes horizontal, and adhering the first diamond grains onto the gripping surface by further depositing a metal containing nickel within the second plating solution onto the gripping surface at a uniform thickness that does not exceed the first grain diameter; placing the gripping tool in the bottom of the second plating solution in such a manner that the gripping surface becomes horizontal after the first diamond grains have been adhered; and placing a plurality of second diamond grains having a second grain diameter smaller than the first grain diameter onto a metal surface of the gripping surface on which the first diamond grains are not present and which is formed by depositing the metal containing nickel, and adhering the second diamond grains onto the metal surface by further depositing the metal containing nickel within the second plating solution onto the metal surface at a uniform thickness that does not exceed the first grain diameter and the second grain diameter until a position relationship between the metal surface and the second diamond grains is not displaced even when the gripping tool is moved.

In a gripping tool according to a second aspect of the present invention, a plurality of first diamond grains having a uniform first grain diameter equal to or smaller than 140 µm are adhered onto a gripping surface by a metal layer containing nickel at a thickness that does not exceed the first grain diameter in a state where the first diamond grains make contact with the gripping surface and are evenly distributed so that tops of the first diamond grains can be aligned, and a plurality of second diamond grains having a second grain diameter smaller than the first grain diameter are adhered by the metal layer containing nickel onto the metal layer containing nickel of the gripping surface, on which the first diamond grains are not present, in a uniform thickness that causes heads of the diamond grains having the first grain diameter and the second grain diameter to protrude.

BRIEF DESCRIPTION OF THE DRAWINGS

FIG. 6C illustrates results of measurements of gripping forces of paper plated according to the present invention, and paper not plated.

FIG. 6D illustrates results of measurements of gripping forces of chicken skin plated according to the present invention, and chicken skin not plated.

DESCRIPTION OF EMBODIMENTS

Figure 10:
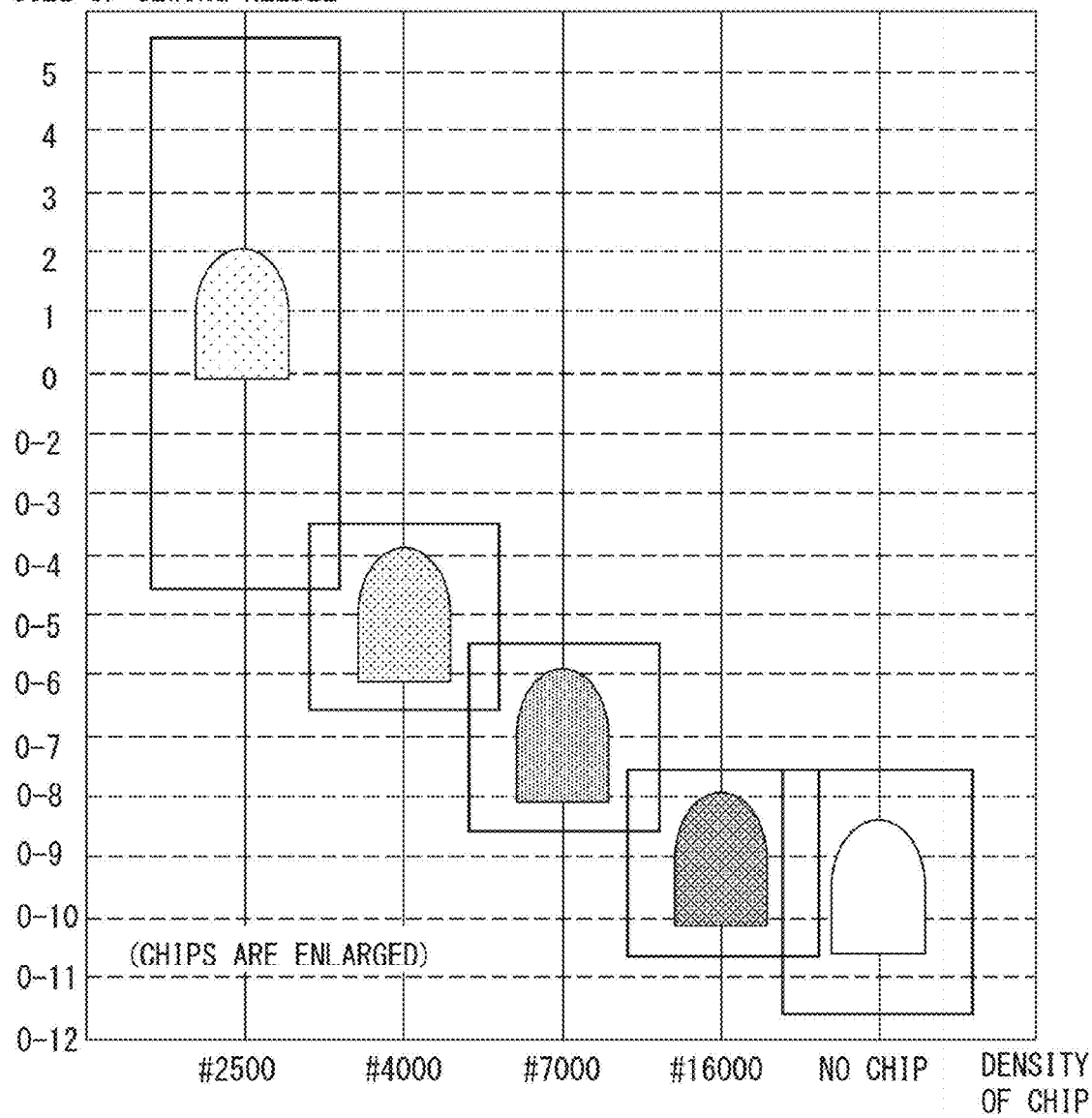
FIG. 10 illustrates gripping surfaces suitable for different sewing needle sizes in a needle holder in a comparison example.

In gripping tools used in neurosurgery, cardiac surgery or the like, the gripping surface has a small area. Therefore, it is difficult to braze onto them protrusions shaped like a square pyramid, and conventional gripping tools have had a flat surface (see "no chips" in FIG. 10). If a gripping surface of a needle holder is flat, it is difficult to stably grip a sewing needle, and the sewing needle can be dropped due to a displacement of a gripping position of the sewing needle during an operation. Moreover, if a gripping surface of micro-tweezers such as forceps or the like is flat, this makes it difficult to securely grip a slippery biological membrane, blood vessel or the like.

Needle holders having a gripping force that was improved by adhering ultra-hard grains such as tungsten carbide or the like onto a gripping surface have been developed in Europe and the US. However, since the ultra-hard grains adhered onto the gripping surface are not dispersed evenly (see FIG. 9C), the gripping force is not sufficient, and a sewing needle can be displaced or dropped. Moreover, if a technique for improving a gripping force by adhering ultra-hard grains such as tungsten carbide or the like onto a gripping surface is applied to micro-tweezers, unevenly adhered ultra-hard grains cannot sufficiently deal with living tissue such as a biological membrane, a blood vessel and the like, leading to a problem in precision and durability.

Embodiments according to the present invention are described in detail below with reference to the drawings.

First Embodiment

FIGS. 1A to 1D are explanatory diagrams No. 1) of the entirety of a plating processing method of a gripping surface of a gripping tool according to an embodiment of the present invention. FIGS. 2A to 2C are explanatory diagrams (No. 2) of the entirety of the plating processing method of a gripping surface of a gripping tool according to the embodiment of the present invention.

The entirety of the plating processing method of a gripping surface of a gripping tool according to the present invention is described in the order of processes illustrated in FIGS. 1A to 1D and 2A to 2C.

Figure 1A:
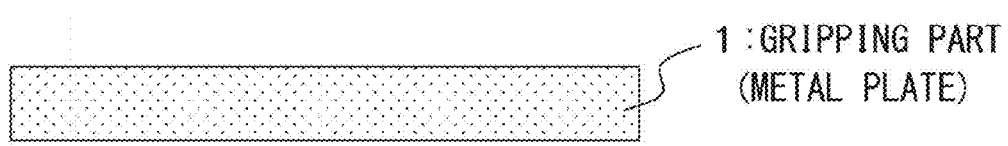
FIG. 1A is an explanatory diagram of a preprocess (degreasing).
Figure 2A:
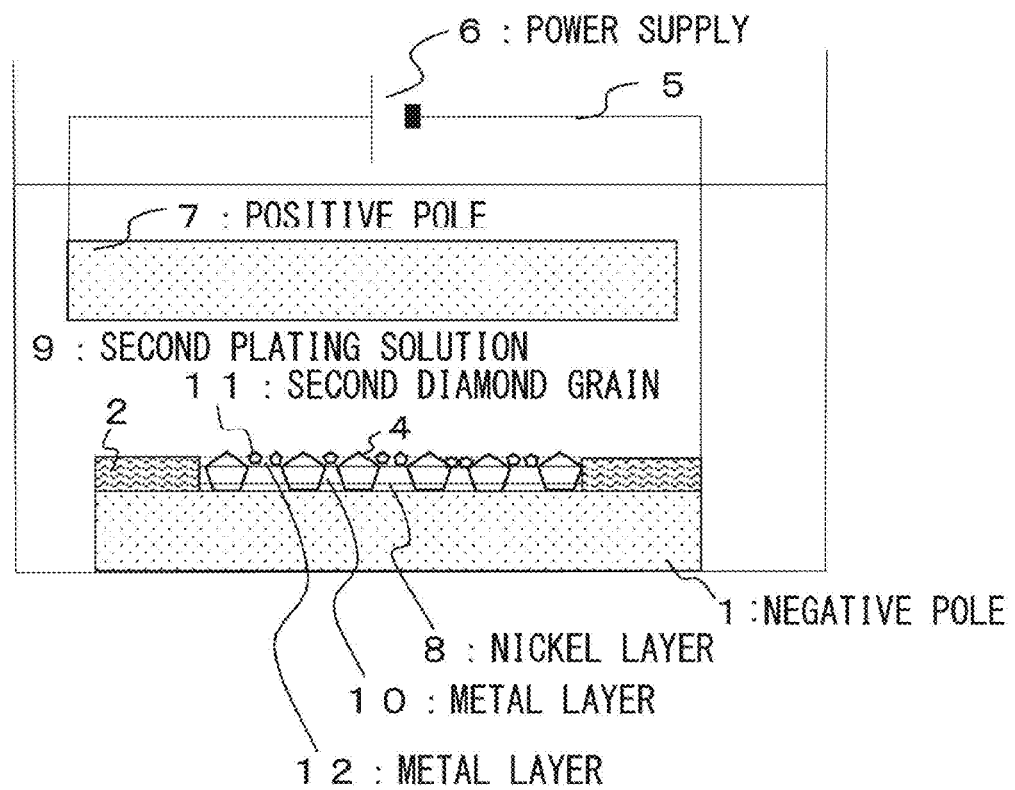
FIG. 2A is an explanatory diagram of a third plating (fixing) process.
Figure 2B:
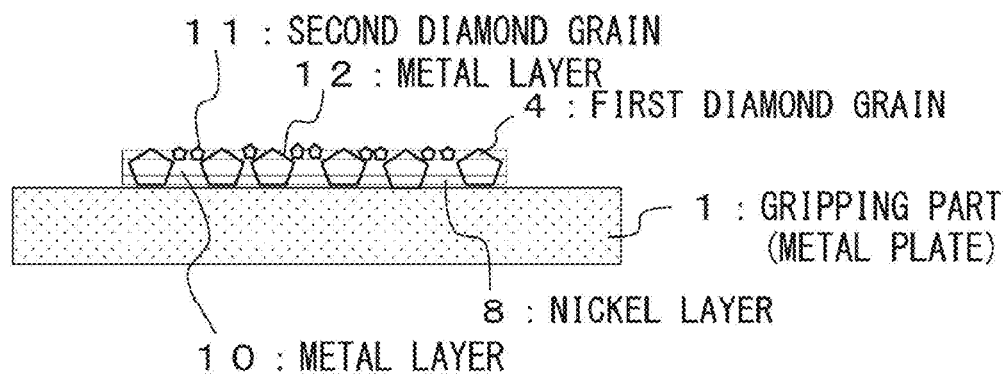
FIG. 2B is an explanatory diagram of a masking removal process.
Figure 2C:
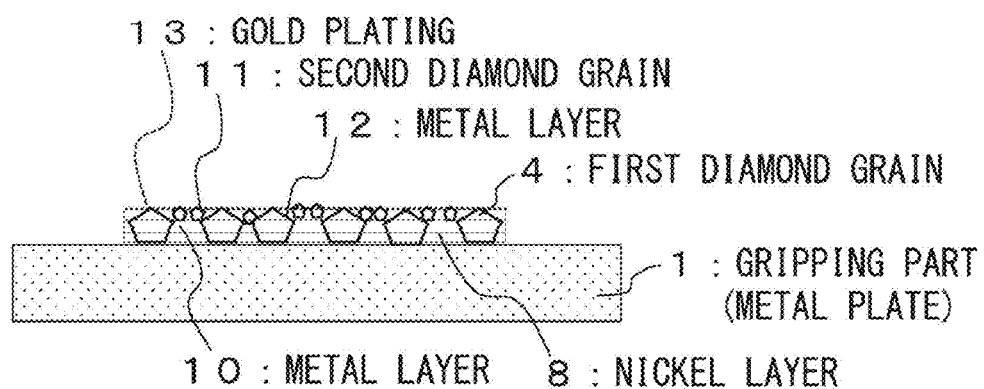
FIG. 2C is a gold plating process.

FIG. 1A illustrates a degreasing process. The degreasing process is a process for removing oil and fat attached to a gripping surface of a gripping part 1 to be plated. The degreasing process may be immersion degreasing that does not use solvent, or degreasing using only an alkaline solution, such as electro degreasing or the like, in addition to solvent degreasing using a chlorinated organic solvent such as trichloroethylene or the like. For an immersion greasing bath, various types of alkaline medicines can be combined and used. However, when degreasing cannot be fully performed with only alkaline immersion greasing, electro degreasing is performed as finish-degreasing.

Figure 1B:
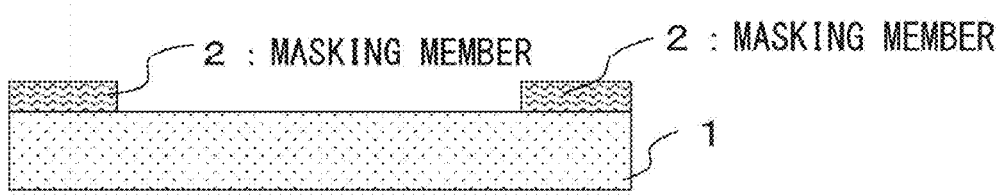
FIG. 1B is an explanatory diagram of a masking process and an acid treatment.

FIG. 1B illustrates a masking process and an acid treatment. The masking process is a process performed to cover a portion on which a plating process is not to be performed, and to cover, with a masking member 2, a portion of a gripping surface on which the plating process is not to be performed. Examples of the masking member 2 include masking tape, a masking coating material, and the like. The acid treatment is a treatment for activating a metal surface. The acid treatment is performed, for example, by immersing a metal plate in a hydrochloric solution of approximately 20 percent.

Figure 1C:
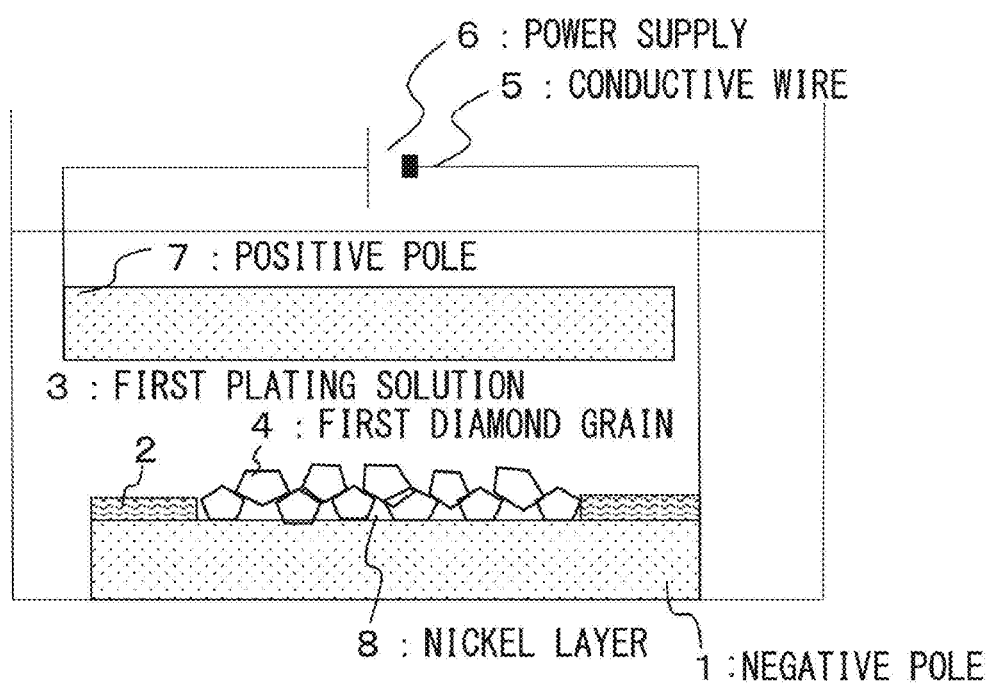
FIG. 1C is an explanatory diagram of a first plating (temporary fixing) process.

FIG. 1C illustrates a first plating (temporary fixing) process. With the first plating (temporary fixing) process, a plurality of first diamond grains 4 having a uniform first grain diameter are placed on a top surface, in a quantity that covers the top surface, of the gripping part 1 (metal plate) that is placed in a bottom of a first plating solution 3, which is an electroplating solution containing nickel as a main ingredient, in a manner such that the gripping surface becomes horizontal. Here, the shape and the grain diameter of the first diamond grains 4 are not particularly limited. However, for example, a shape such as a regular hexahedron is preferable, and a first grain diameter of several μm to 140 μm is preferable. Here, variations in the grain diameter are as uniform as a normally acceptable level at which diamond grains can be screened. Diamond grains are screened, for example, pursuant to the JIS B 4130-1982 standard (a grain size of diamond or cubic boron nitride). Compositions of the first plating solution 3 include, for example, nickel sulfate, $NiSO_4.6H_2O$; nickel chloride, $NiCl_2.6H_2O$; nickel sulfamate; an additive agent; and the like The gripping part 1 placed in the bottom of the first plating solution 3 is connected to a power supply 6, for example, via a conductive wire 5, and a positive pole 7 that is composed of nickel and is provided on a top or a side of the first plating solution 3, and the gripping part 1 is implemented as a negative pole. By performing electroplating in a state where the gripping part 1 is made to be stationary, nickel is deposited onto the gripping surface until the gripping part 1 within the first plating solution 3 is not displaced despite being moved. Then, the first diamond grains 4 are temporarily fixed onto the gripping surface by forming a nickel layer 8 on a surface of the gripping surface other than the surface with which the first diamond grains 4 on the gripping surface make contact. A thickness of the nickel layer 8 at this time is, for example, 5 μm.

In the first plating (temporary fixing) process, a distribution density is adjusted to a desired density by adjusting the first grain diameter, a duration of temporary fixing, the amount of an electric current, or the like. If the distribution density of the first diamond grains is increased, the gripping force becomes more uniform across all positions on the gripping surface. This is preferable, for example, for a needle holder that grips a sewing needle or a suture thread. Moreover, the gripping force for a living tissue is improved by suitably decreasing the distribution density of the first diamond grains 4. This is suitable for micro-tweezers such as forceps or the like.

Figure 1D:
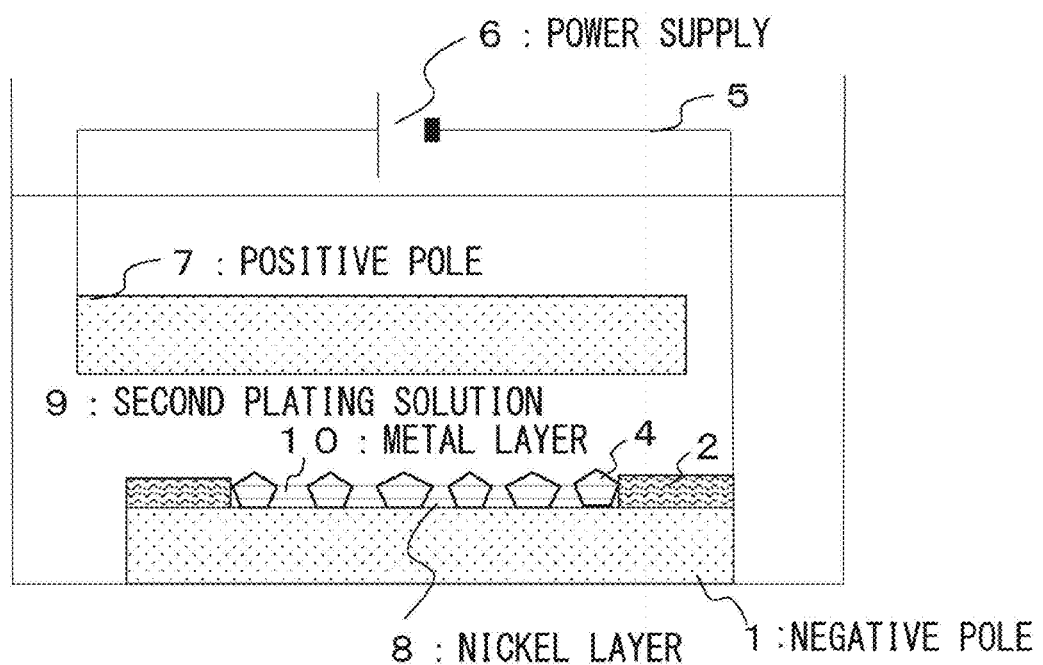
FIG. 1D is an explanatory diagram of a second plating (fixing) process.

Next, redundant first diamond grains 4 that are not temporarily fixed are removed after the first plating (temporary fixing) process illustrated in FIG. 1C, and the method proceeds to a second plating (fixing) process illustrated in FIG. 1D. The second plating (fixing) process is a process for securely fixing, onto the gripping surface, the first diamond grains 4 that have been temporarily fixed with the first plating (temporary fixing) process.

As illustrated in FIG. 1D, the gripping part 1 from which the redundant first diamond grains 4 have been removed is placed in a bottom of the electroplating solution containing nickel ion as a main ingredient or in a second plating solution 9, which is an electroless plating solution intended to form a nickel alloy film with auto catalysis, in such a manner that the gripping surface becomes horizontal. Preferably, a metal is deposited by using both electroplating and electroless plating so that the thickness of the nickel layer 8 and the metal layer 9 from the gripping surface cannot exceed the first grain diameter of the first diamond grains 4, and the thickness can become, for example, approximately 55 to 65 percent of the first grain diameter.

FIG. 1D illustrates the state where the positive pole 7 and the gripping part 1 are connected to the power supply 6 via the conductive wire 5. This figure represents the case of electroplating. A material of the positive pole 7 is selected to suit the compositions of the second plating solution 9. In the case of the electroless plating, the conductive wire 5, the power supply 6 and the positive pole 7 are not needed, and a temperature of the solution 9 is kept at 60 to 90° C., and a metal is deposited with autocatalysis. With electroplating, a speed at which a metal containing nickel is deposited on the surface of the negative pole 1 can be adjusted by regulating the amount of a current flowing between the positive pole 7 and the negative pole 1. In the meantime, with the electroless plating, a metal containing nickel is deposited onto the gripping part 1 without applying an electric current. Both the electroplating and the electroless plating are used, so that a metal layer 10 having an even thickness can be formed.

In both the first plating (temporary fixing) process illustrated in FIG. 1C and the second plating (fixing) process illustrated in FIG. 1D, it is preferable to adjust the concentration of a nickel solution, a surface-active agent or the like added to prevent diamond grains from being aggregated.

Examples of compositions of the second plating solution 9 as an electroplating solution include nickel sulfate, $NiSO_4.6H_2O$; nickel chloride, $NiCl_2.6H_2O$; nickel sulfamate, $Ni(NH_2SO_3)_2$; cobalt sulfate $CoSO_4$; boric acid $H_3BO_3$; an additive agent; and the like. Alternatively, when the electroless plating is used as the second plating process, an electroless plating solution that forms a Ni—P alloy plating film, a Ni—P—Co alloy plating film, a Ni—W alloy plating film, a Ni—B—W alloy plating film, or a Ni—P—B—W alloy plating film may be used. Moreover, both the electroplating process and the electroless plating process are used, so that a multi-layer film of nickel, and a nickel alloy such as a Ni—P alloy, a Ni—Co alloy, a Ni—W alloy, a Ni—B—W alloy, a Ni—P—B alloy or the like can be formed. By forming a multi-layer film of a nickel alloy, the holding force of diamond grains is improved.

FIG. 2A illustrates a third plating (fixing) process. The third plating (fixing) process is a process for adhering a plurality of second diamond grains 11 onto the top surface of the gripping part 1 (metal plate) by placing, in troughs between peaks of the first diamond grains 4 that are evenly adhered, the plurality of second diamond grains 11 having a second grain diameter smaller than the first grain diameter, and by depositing a metal containing nickel to form a metal layer 12. A thickness of the metal layer 12 in this case is a thickness that does not exceed the second grain diameter. For example, a thickness of approximately 55 to 65 percent of the second grain diameter is preferable.

Here, the second grain diameter is, preferably, one-tenth, one-third or the like of the first grain diameter. When the second grain diameter is one-tenth of the first grain diameter, the second diamond grains 11 are adhered by forming the metal layer 12 onto the metal layer 10 with the third plating (fixing) process illustrated in FIG. 2A. Alternatively, when the second grain diameter is one-third of the first grain diameter, the second diamond grains 11 are adhered by performing the third plating (fixing) process illustrated in FIG. 2A after the first plating (temporary fixing) process illustrated in FIG. 1C has been performed for the second diamond grains 11 subsequently to the second plating (fixing) process illustrated in FIG. 1D.

By performing the third plating process, heads (tops) of the first diamond grains 4 that are adhered onto the gripping surface and have a large grain diameter can be aligned with heads (tops) of the second diamond grains 11 having a small grain diameter. By aligning the heads of the first diamond grains 4 with the heads of the second diamond grains 11, a substantial area of contact is increased. As a result, the gripping force in the entire region within the gripping surface increases uniformly, a stable gripping characteristic can be achieved, and the area of a metal layer exposed to the surface is reduced, whereby wear resistance can be improved.

Note that the heads of the second diamond grains 11 having a small grain diameter may be aligned at a position lower than the heads of the first diamond grains 4 that are adhered onto the gripping surface and have a large grain diameter, when the third plating process is performed. Thus, the gripping force that grips a living tissue such as a biological membrane, a blood vessel or the like is improved. This is preferable for a plating process of a gripping surface of a gripping tool that grips a living tissue such as a biological membrane, a blood vessel or the like.

FIG. 2B illustrates a masking removal process. After the process for adhering the first diamond grains 4, or the first diamond grains 4 and the second diamond grains 11 onto the gripping part (metal plate) 1 has been terminated, a masking tape or a masking material is removed.

FIG. 2C illustrates a gold plating process. On a surface where the second plating process, or the second plating process and the third plating process, have been performed, gold plating is performed. The gold-plated gripping surface can avoid a biological reaction of nickel. Accordingly, gold plating is preferable, for example, as a surface treatment of a tool such as a needle holder, micro-tweezers (forceps), or the like, which are medical gripping tools. Here, performing gold plating on a gripping tool also functions as a marker that indicates the gripping tool on which the plating process according to the present invention was performed. Note that platinum, rhodium or the like may be used as a replacement for gold as a plating metal that avoids a biological reaction of nickel.

A relationship between a gripping force and a frictional coefficient is described below.

Figure 3A:
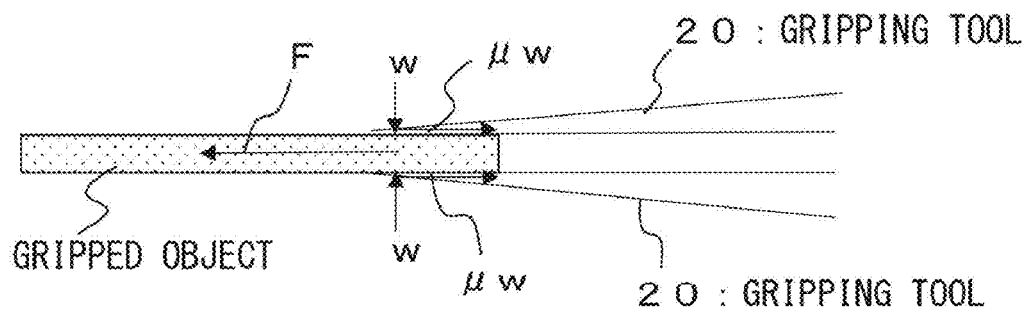
FIG. 3A is an explanatory diagram of a gripping force applied when an object is gripped by a gripping tool.
Figure 3B:
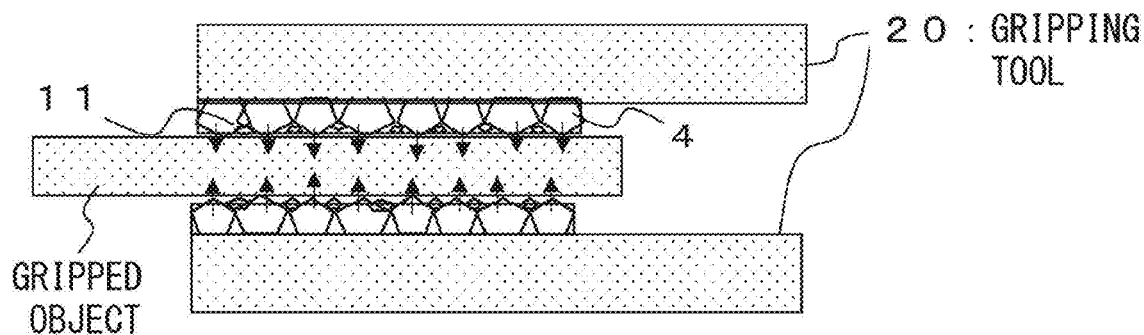
FIG. 3B is an enlarged conceptual view of a gripping surface when the object is lightly gripped.
Figure 3C:
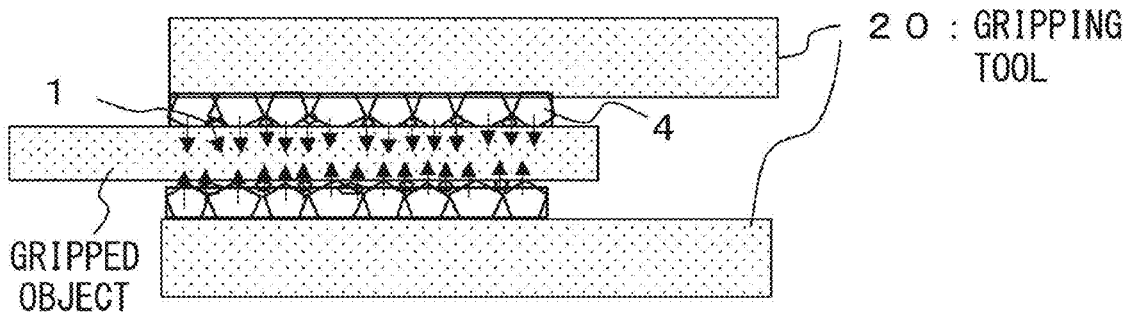
FIG. 3C is an enlarged conceptual view of the gripping surface when the object is tightly gripped.

FIGS. 3A to 3C are explanatory diagrams of a relationship between a frictional force of a gripping surface and a gripping force. FIG. 3A is an explanatory diagram of the gripping force applied when an object is gripped by a gripping tool. FIG. 3B is an enlarged view of a gripping surface when the object is lightly gripped. FIG. 3C is an enlarged view of a gripping surface when the object is tightly gripped.

As illustrated in FIG. 3A, the object is gripped by the gripping tool 20 with a force having a load w in the vertical direction. When the object is pulled in a leftward direction with a tension F, the gripping tool 20 pulls the gripped object in a rightward direction with a frictional force.

In this specification, when the force is increased that pulls the object in the rightward direction by the gripping tool 20 while the load w(gw) with which the gripping tool 20 grips the object in the vertical direction is kept constant, a pulling force F(gw) applied when the gripped object starts to slide is defined as the gripping force. Assuming that the load applied from a tip portion to a gripped object and a frictional coefficient are respectively "w" and "μ", the gripping force F of the gripping tool is represented as follows because the object is gripped with both of the tip portions.

$$F = 2 \times \mu w \qquad (1)$$

According to the formula (1), it is proved that the gripping force F of the gripping tool is increased by increasing the frictional coefficient μ.

As illustrated in FIG. 3B, when the object is lightly gripped by the gripping tool 20, the gripped object makes contact with the gripping surface of the gripping tool 20 only at the peaks of the first diamond grains 4 adhered onto the gripping surface of the gripping tool 20. In the meantime, as illustrated in FIG. 3C, when the object is tightly gripped by the gripping tool 20, the gripped object makes contact with the gripping surface of the gripping tool 20 at both the peaks of the first diamond grains 4 and the peaks of the second diamond grains 11.

Making a comparison between FIGS. 3B and 3C, it can be considered also that the frictional coefficient μ increases with an increase in the area of contact when the load w applied from the gripping tool 20 to the gripped object is increased.

In FIG. 3B, when the gripped object is a rigid body shaped like a plate or a bar, the area of contact remains unchanged even if the load w applied from the gripping tool 20 to the gripped object is increased. Therefore, it can be considered that the frictional coefficient μ is almost constant.

In the meantime, when a living tissue such as a biological membrane, a blood vessel or the like is gripped, the shape of the gripped object varies as the magnitude of the gripping force increases. Since the area of contact increases, it can be considered that the frictional coefficient μ becomes a larger value.

Additionally, in the living tissue such as a biological membrane, a blood vessel or the like, a viscous liquid such as blood, a lymph fluid or the like is attached to the gripping surface of the gripping tool. Therefore, it can be considered that the gripping force F of the gripping tool used in an actual medical setting relates to a sum of the load w applied from the gripping tool 20 to the gripped object and an adhesion force generated from a viscous fluid such as blood, a lymph fluid or the like.

Layer structures of the gripping surfaces are described below.

Figure 4A:
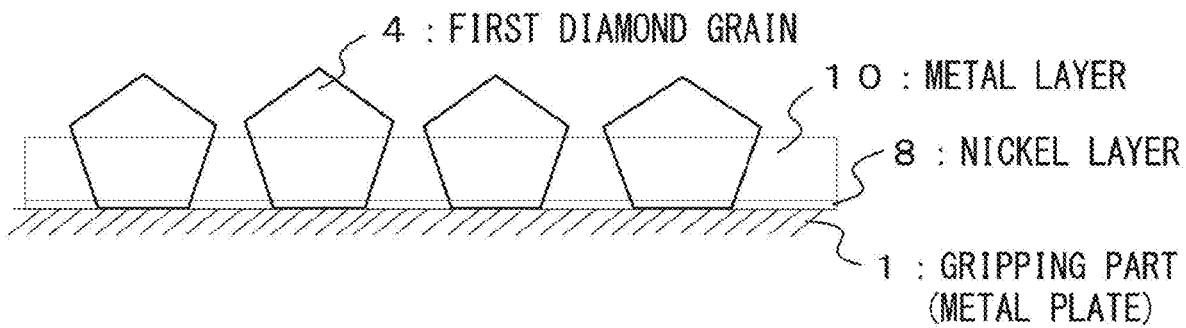
FIG. 4A illustrates an example of a structure of a cross section of the gripping surface onto which only first diamond grains are adhered.
Figure 4B:
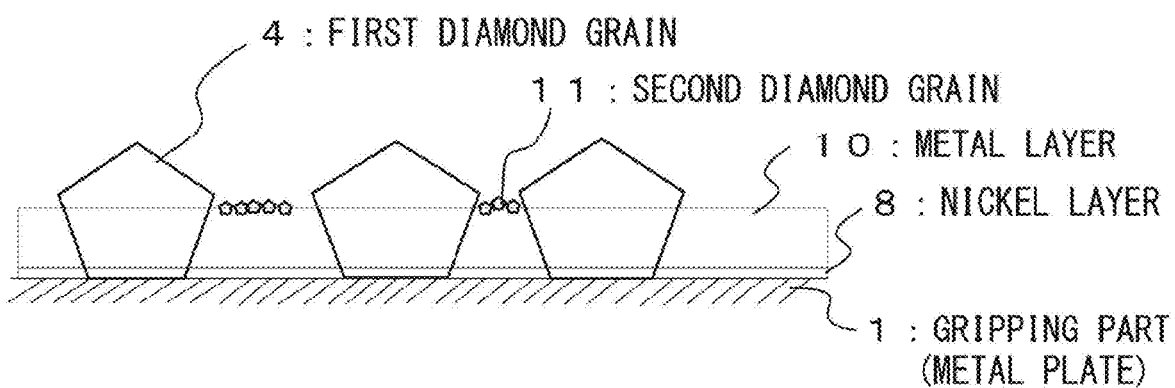
FIG. 4B illustrates a structure of a cross-sectional layer of the gripping surface onto which a second grain diameter and the first diamond grains and second diamond grains are adhered. (The second particle size≈first particle size/10)
Figure 4C:
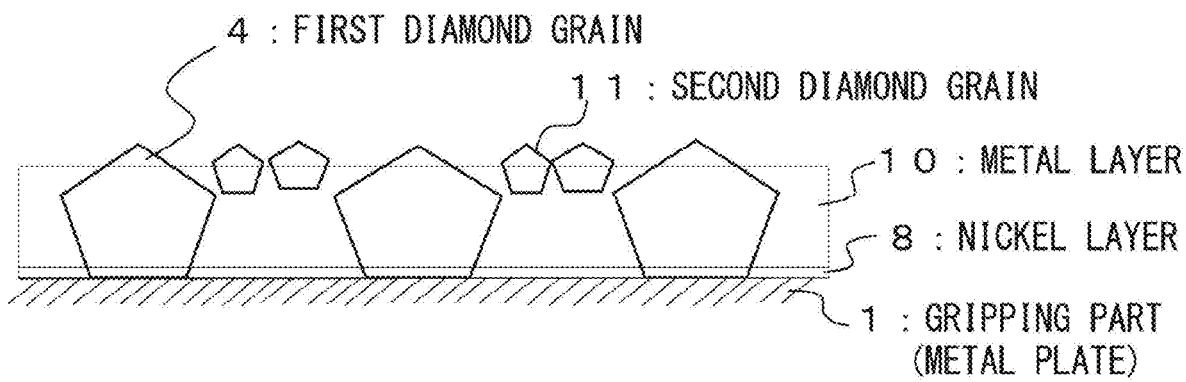
FIG. 4C illustrates a structure of a cross-sectional layer of the gripping surface onto which the first diamond grains and the second diamond grains are adhered. (The second particle size≈first particle size/3)

FIGS. 4A to 4C are explanatory diagrams of layer structures of diamond grains adhered onto a gripping surface where the plating processing method according to the embodiment of the present invention was performed. In FIGS. 4A to 4C, the metal layer 12 and the gold plating 13 that are illustrated in FIGS. 2A to 2C are omitted for ease of understanding.

FIG. 4A illustrates an example of a structure of a cross section when only the first diamond grains 4 are adhered. In the structure of the cross section illustrated in FIG. 4A, the plurality of first diamond grains 4 are adhered onto the gripping surface by a metal layer having a thickness of 55 to 65 percent of the first grain diameter in a state where the heads (tops) of the first diamond grains 4 are aligned. Since the heads (tops) of the first diamond grains 4 adhered onto the gripping surface are aligned, a stable gripping force can be achieved on the entire gripping surface.

FIG. 4B illustrates an example of a structure of a cross section of the gripping surface onto which the first diamond grains 4 and the second diamond grains 11 having a second grain diameter of one-tenth of the first grain diameter are adhered. In the structure of the cross section illustrated in FIG. 4B, the plurality of second diamond grains 11 are adhered at a position lower than the position of the heads of the plurality of first diamond grains 4 in such a state that the heads (tops) of the second diamond grains 11 are aligned between the first diamond grains 4, which are adhered in a state where the heads (tops) of the first diamond grains 4 are aligned. In the example of the structure of the cross section illustrated in FIG. 4B, the heads (tops) of the first diamond grains 4 are aligned when the object is lightly gripped. Therefore, a stable gripping force can be obtained on the entire gripping surface. Alternatively, when the object is tightly gripped, the second diamond grains are adhered at the position lower than the position of the heads of the first diamond grains 4 in the state where the heads (tops) of the second diamond grains 11 are aligned. Accordingly, a high gripping force can be exerted since spaces are present on the gripping surface which a biological tissue works its way into. The second diamond grains 11 cover the metal layer 12 exposed at the surface, whereby wear resistance can be improved.

FIG. 4C illustrates an example of a structure of a cross section of the gripping surface onto which the first diamond grains 4 and the second diamond grains 11 having a second grain diameter of one-third of the first grain diameter are adhered. In the structure of the cross section illustrated in FIG. 4C, the first diamond grains 4 and the second diamond grains 11 are adhered in a state where the heads (tops) of both the first diamond grains 4 and the second diamond grains 11 are aligned. In the example of the structure of the cross section illustrated in FIG. 4C, the heads (tops) of both the first diamond grains 4 and the second diamond grains 11 that are adhered onto the gripping surface are aligned. Therefore, an actual area of contact with a gripped object increases, so that a more stable gripping force than that in the structure of the cross section illustrated in FIG. 4A can be achieved on the entire gripping surface.

Evaluations of the gripping tool on which the plating process according to the present invention was performed are described below.

Figures 5A, 5B:
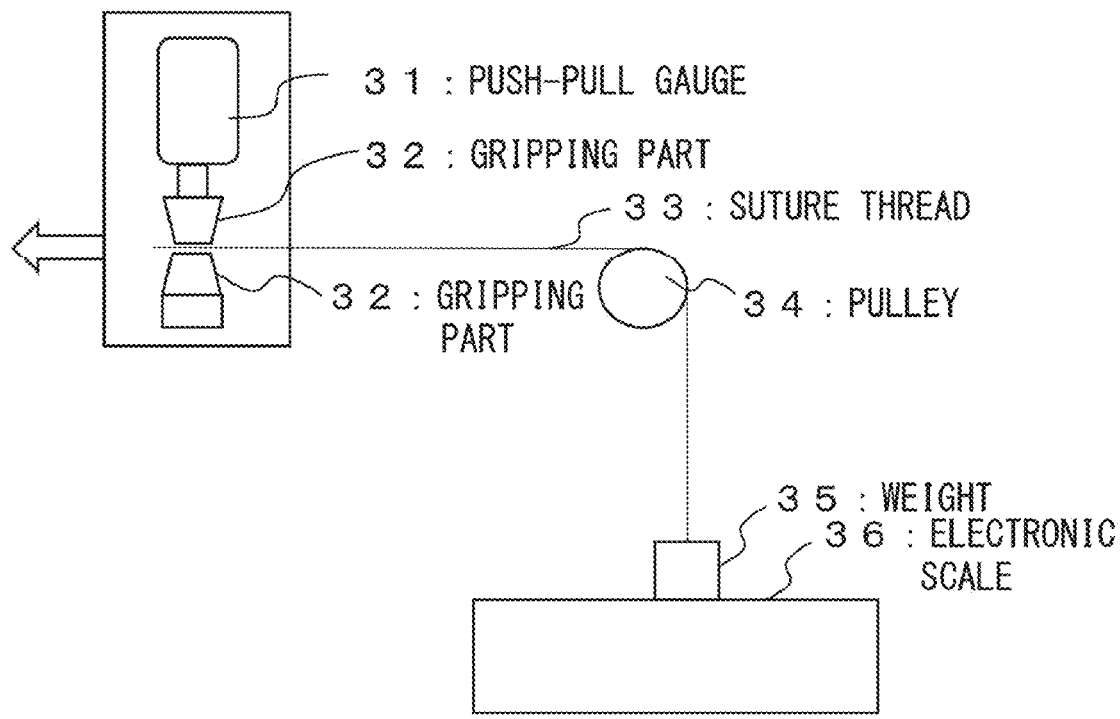
FIG. 5A is an explanatory diagram of a gripping force measurement method of a suture thread.
FIG. 5B illustrates results of measurements (of a suture thread) of gripping forces of a product plated according to the present invention, and a product not plated.

A method of a gripping force measurement test, and results of the measurement of the gripping force, are described with reference to FIGS. 5A, 5B and 6A to 6D. FIGS. 5A and 5B respectively illustrate an explanation of a method for measuring a gripping force of a suture thread, and results of a measurement according to the present invention and a measurement of a comparison example.

FIG. 5A is an explanatory diagram of the method for measuring a gripping force of a suture thread.

A push-pull gauge 31 is configured so that a pinching load with which a gripping part 32 pinches a suture thread 33 can be measured. The gripping surface of the gripping part 32 takes the shape of a circle having a diameter of 1.5 mm, and has a circular area set to φ1.5. Moreover, as the suture thread 33, a suture thread having a standard thickness of a diameter of 0.148 mm is used.

A leftward force is applied to the push-pull gauge 31 in a state where the suture thread 33 is gripped by the gripping part 32, and an upward force is applied to a weight 35 of 25 g via a pulley 34. The weight 35 is placed on an electronic scale 36, and is provided to detect that the weight 35 starts to move in an upward direction.

The pinching load applied when the electronic scale 36 detects that the weight 35 starts to move in the upward direction due to applying a force in the leftward direction to the push-pull gauge 31 while changing the pinching load with which the gripping part 32 pinches the suture thread 33 was measured.

FIG. 5B illustrates results of a measurement of a pinching load applied to an unprocessed gripping surface of a gripping part equivalent to an existing product, and results of a measurement of the gripping surface on which only the first diamond grains having a grain diameter of 30 μm or 50 μm are adhered and the plating process according to the present invention was performed. In FIG. 5B, for the unprocessed gripping surface of the gripping part equivalent to the existing product, the pinching load needed to lift a weight of 20 g is approximately 60 g. In the meantime, for the gripping surface on which the diamond grains having a grain diameter of 30 μm are adhered and the plating process according to the present invention was performed, a pinching load needed to lift a weight of 20 g is approximately 5.0 g. For the gripping surface on which the diamond grains having a grain diameter of 50 μm are adhered and the plating process according to the present invention was performed, a pinching load needed to lift a weight of 20 g is approximately 4.0 g. Namely, for both of the gripping surfaces on which the diamond grains having a grain diameter of 30 μm or 50 μm are adhered and the plating process according to the present invention was performed, the pinching load needed to lift a weight of 20 g is approximately one tenth of the pinching load of the unprocessed gripping surface of the gripping part equivalent to the existing product.

In other words, the frictional coefficient μ of the gripping surface on which the plating process according to the present invention was performed is approximately ten times the frictional coefficient of the unprocessed gripping surface of the gripping part equivalent to the existing product.

FIGS. 6A to 6D illustrate an explanation of a gripping force measurement method of stainless steel foil, paper and chicken skin, and results of measurements of the method according to the present invention and a comparison example.

Figures 6A, 6B:
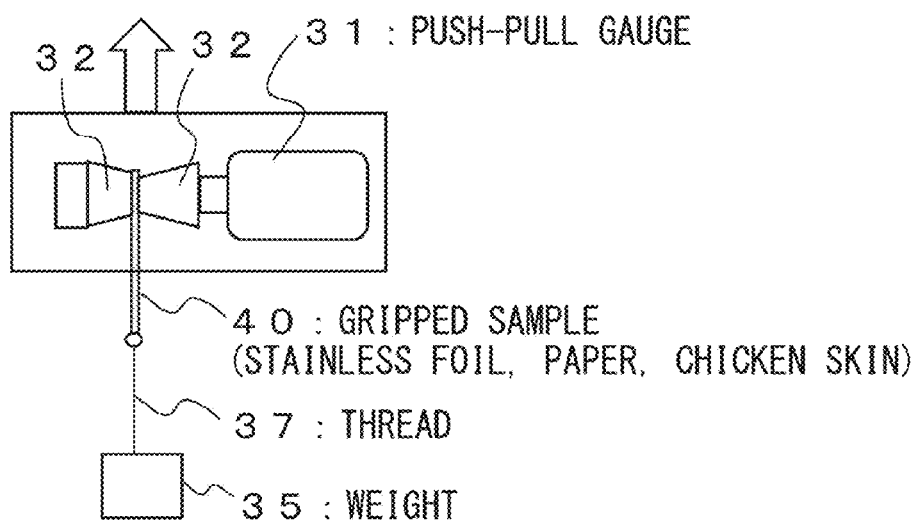
FIG. 6A is an explanatory diagram of a gripping force measurement method of stainless steel foil, paper and chicken skin.
FIG. 6B illustrates results of measurements of gripping forces of stainless steel foil plated according to the present invention and stainless steel foil not plated.

FIG. 6A is an explanatory diagram of the method for measuring a gripping force of a gripped sample (stainless steel foil, paper or chicken skin).

The push-pull gauge 31 is configured so that a pinching load with which the gripping part 32 pinches the gripped sample (stainless steel foil, paper or chicken skin) 40 processed in the shape of a strip can be measured. The gripping surface of the gripping part 32 takes the shape of a circle having a diameter of 1.5 mm, and has a circular area set to φ1.5. The weight 35 is attached to one end of a thread 37 made of 100% polyester so that no load can be applied, the other end of the thread 37 is secured to the strip-shaped gripped sample 40, and the gripped sample 40 is pinched by the gripping part 32 with an arbitrary pinching load. Thereafter, whether the weight 35 can be continuously held after the weight 35 has been freed is observed. A pinching load applied when the weight 35 cannot be held any more when the pinching load is changed was measured by the push-pull gauge 31.

FIG. 6B illustrates results of measurements of a pinching load of the gripped sample 40 of 1 cm×1.5 cm of stainless steel foil (MISUMI SUS304H Shim Tape 370 to 420HV with a thickness of 0.003 mm) for an unprocessed gripping surface of a gripping part equivalent to the comparison example, and also a pinching load of the gripped sample 40 for a gripping surface on which the plating process according to the present invention was performed.

In the comparison example, a pinching load needed to pinch the stainless steel foil in order to continuously hold a weight of 50 g is approximately 190 g. In the meantime, for the gripping surface on which the diamond grains having a grain diameter of 30 μm or 50 μm are adhered and the plating process according to the present invention was performed, a pinching load needed to lift a weight of 50 g is approximately 60 g. Namely, for both of the gripping surfaces on which the diamond grains having a grain diameter of 30 μm or 50 μm are adhered and the plating process according to the present invention was performed, the pinching load of the stainless steel foil needed to lift a weight of 50 g is approximately one-third of the pinching load of the unprocessed gripping surface of the gripping part equivalent to the existing product.

FIG. 6C illustrates results of measurements of a pinching load of the gripped sample of 1 cm×1.5 cm of paper (copy paper GAAA 5009 made by FUJI Xerox with a thickness of 0.08 mm) for the unprocessed gripping surface of the gripping part equivalent to the comparison example, and also a pinching load of the gripped sample for the gripping surface on which the diamond grains having a grain diameter of 30 μm or 50 μm are adhered and the plating process according to the present invention was performed.

In the comparison example, the pinching load needed to pinch the paper in order to continuously hold a weight of 50 g is approximately 135 g. In the meantime, for the gripping surface on which the diamond grains having a grain diameter of 30 μm or 50 μm are adhered and the plating process according to the present invention was performed, the pinching force needed to lift a weight of 50 g is approximately 45 g. Namely, for both of the gripping surfaces on which the diamond grains having a grain diameter of 30 μm or 50 μm are adhered and the plating process according to the present invention was performed, the pinching load of the paper needed to lift a weight of 50 g is approximately one-third of the pinching load of the unprocessed gripping surface of the gripping part equivalent to the existing product.

FIG. 6D illustrates results of measurements of a pinching load of the gripped sample of 2 cm×2 cm of chicken skin (a partial skin of a spring chicken produced in Yamagata Prefecture with an even thickness of 0.1 to 0.15 mm) for an unprocessed gripping surface of the gripping part equivalent to the comparison example, and also a pinching load of the gripped sample for the gripping surface on which the first diamond grains having a grain diameter of 30 μm or 50 μm are adhered and the plating process according to the present invention was performed.

In the comparison example, the pinching load needed to pinch the chicken skin in order to continuously hold a weight of 20 g is approximately 160 g. In the meantime, for the gripping surface on which the diamond grains having a grain diameter of 30 μm are adhered and the plating process according to the present invention was performed, the pinching load needed to lift a weight of 20 g is approximately 40 g, and for the gripping surface on which the diamond grains having a grain diameter of 50 μm are adhered and the plating process according to the present invention was performed, the pinching load needed to lift a weight of 20 g is approximately 20 g.

For the gripping surface on which the diamond grains having a grain diameter of 30 μm are adhered and the plating process according to the present invention was performed, the pinching load of the chicken skin needed to lift a weight of 20 g is approximately one-fourth of the pinching load on the unprocessed gripping surface of the gripping part equivalent to the existing product. Moreover, for the gripping surface on which the diamond grains having a grain diameter of 50 μm are adhered and the plating process according to the present invention was performed, the pinching load of the chicken skin needed to lift a weight of 20 g is approximately one-eighth of the pinching load on the unprocessed gripping surface of the gripping part equivalent to the existing product.

Effects of the plating process method for a gripping surface of a gripping tool according to the present invention are described below.

With the plating processing method of a gripping surface of a gripping tool according to the present invention, a plurality of first diamond grains can be evenly and securely adhered so that heads of the first diamond grains having a uniform first grain diameter can be aligned. Accordingly, stainless steel foil, paper, a suture thread and chicken skin respectively having different hardness can be gripped with a weak force of approximately one-third to one-tenth of the gripping force of the comparison examples in which the plating process is not performed.

Second Embodiment

Needle holders to which the plating processing method according to the present invention is applied are described below.

Figure 7A:
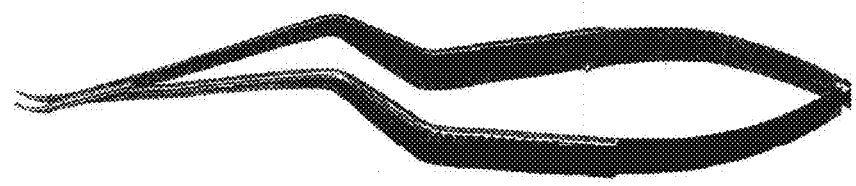
FIG. 7A is a photograph that represents one example of a micro needle holder.
Figure 7B:
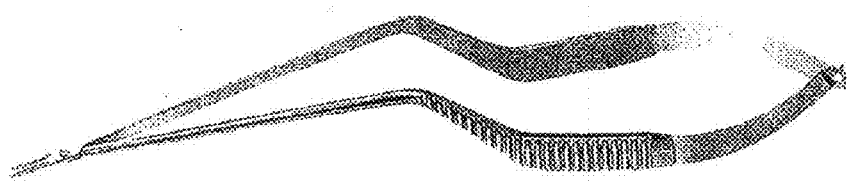
FIG. 7B is a photograph that represents one example of a micro needle holder for a deep portion.

FIGS. 7A and 7B are photographs representing examples of a needle holder as a gripping tool on which the plating process according to the embodiment of the present invention is preferably performed.

A micro needle holder illustrated in FIG. 7A is one example of a needle holder that grips a sewing needle or a suture thread used in an operation of neurosurgery, cardiac surgery or the like. A micro needle holder for a deep portion illustrated in FIG. 7B is a needle holder for an operation used in a deep portion in neurosurgery, and especially in the pituitary gland or the like, and in totality the needle holder has a lengthy form.

The micro needle holders illustrated in FIGS. 7A and 7B have a gripping part at a tip, and the rear of a portion that a doctor grips via a supporting point is formed with an elastic body such as a plate spring or the like. Moreover, the micro needle holders have a lock mechanism for gripping and holding a sewing needle.

The needle holders grip a sewing needle with a gripping part at a tip, and are used by winding a suture thread around the gripping part. Accordingly, diamond grains are adhered (firmly fixed) onto the gripping surface of the gripping part, and it is necessary that diamond grains not be adhered onto portions other than the gripping surface. When diamond grains are adhered onto a portion other than the gripping surface, a suture thread wound around the gripping part can be damaged and cut. With the above describe masking process (see FIG. 1B) and first to third plating processes (see FIGS. 1C, 1D and 2A), diamond grains are adhered only onto the gripping surface of the gripping part.

As illustrated in FIGS. 7A and 7B, by performing the plating process according to the present invention for adhering diamond grains onto a gripping surface on an inner side of the gripping part located at a tip of a micro-needle holder, a pinching load applied to a portion that a doctor grips in order to grip a living tissue such as a biological membrane, a blood vessel or the like is reduced to approximately one-third of the pinching load of the needle holder in the comparison example. Thus, the plating process according to the present invention is preferable as a plating process for a gripping surface of a needle holder of microsurgery that is used for an operation of neurosurgery, cardiac surgery or the like.

Figure 8A:
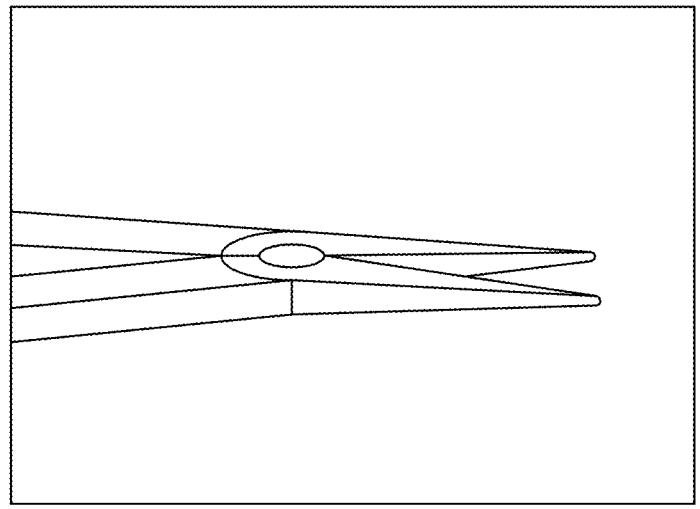
FIG. 8A is a photograph that represents a needle holder on which the plating process according to the present invention was performed.
Figure 8B:
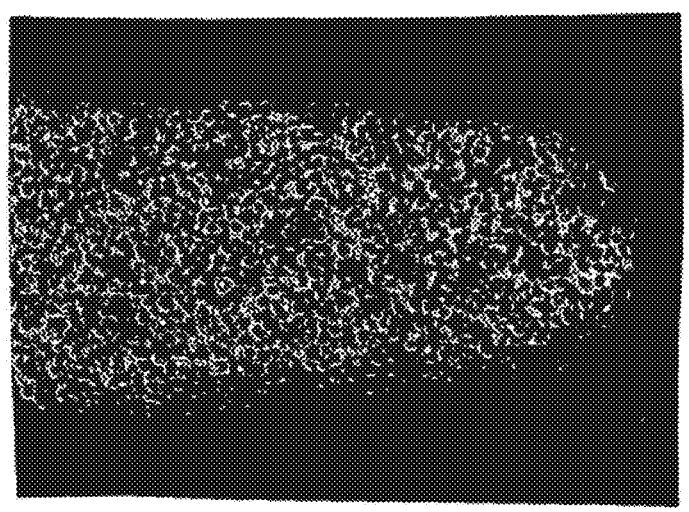
FIG. 8B is an enlarged photograph of the gripping surface of the needle holder of the present invention.

FIG. 8A is a photograph that represents an example of a needle holder on which the plating process according to the embodiment of the present invention was performed. FIG. 8B is an enlarged photograph of the gripping surface of the needle holder on which the plating process according to the embodiment of the present invention was performed.

Figure 9A:
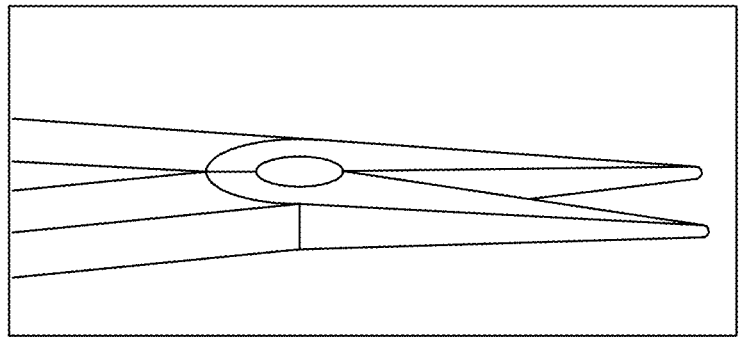
FIG. 9A is a photograph that represents an existing needle holder (onto which ultra-hard powder is brazed).
Figure 9B:
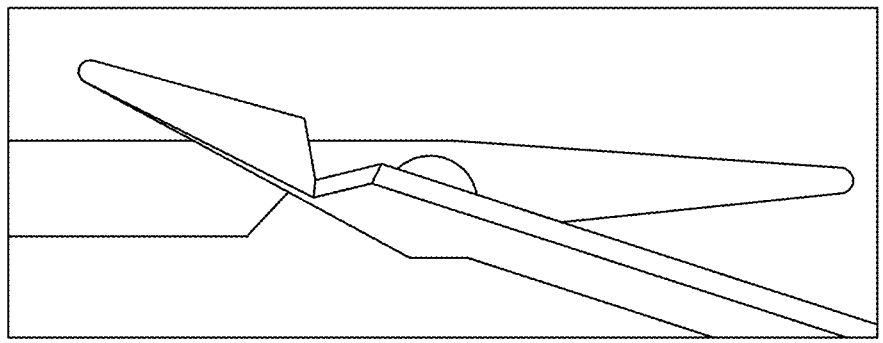
FIG. 9B is a photograph that represents a state where the existing needle holder is opened.
Figure 9C:
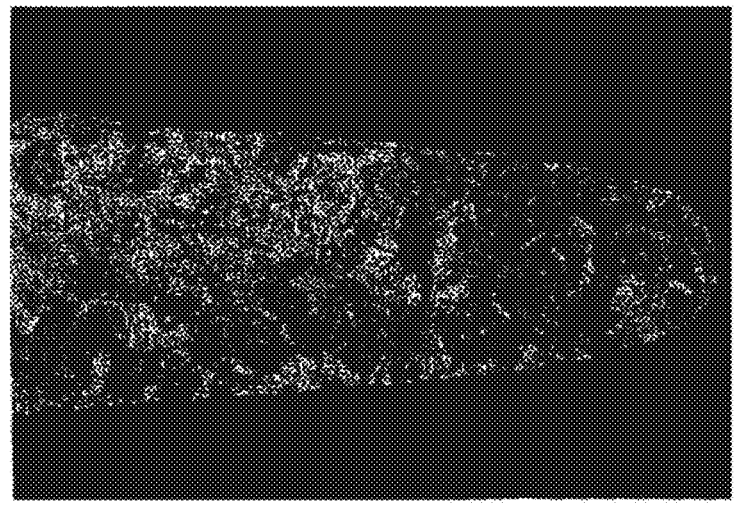
FIG. 9C is an enlarged photograph of a gripping surface of the existing needle holder.

FIG. 9A is a photograph that represents an existing needle holder onto which powder of ultra-hard grains are brazed. FIG. 9B is a photograph in a state where the existing needle holder is opened. FIG. 9C is an enlarged photograph of the gripping surface of the needle holder in the comparison example.

In the enlarged photograph illustrated in FIG. 8B, diamond grains are evenly dispersed, and a state where the unevenness is delicate and uniform is observed. In the meantime, in the enlarged photograph illustrated in FIG. 9, diamond grains are not identified on the gripping surface of the existing needle holder onto which the powder of ultra-hard grains are brazed, and a state where unevenness on the gripping surface is coarse is observed.

Effects of the needle holders in the embodiments are described below.

As illustrated in FIGS. 8B and 9C, it can be anticipated that the needle holders on which the plating process according to the present invention was performed can grip a sewing needle or a suture thread even if a pinching load applied to a gripped portion is small in comparison with the needle holders of the comparison examples onto which the powder of ultra-hard grains is brazed.

Additionally, the hardness of diamond grains adhered onto the gripping surface of the needle holder on which the plating process according to the present invention was performed is approximately four times the hardness of tungsten carbide. Therefore, the needle holders on which the plating process according to the present invention was performed are superior to the needle holders of the comparison examples in wear resistance.

Third Embodiment

Tweezers to which the plating processing method according to the present invention are applied is described below.

Figure 11A:
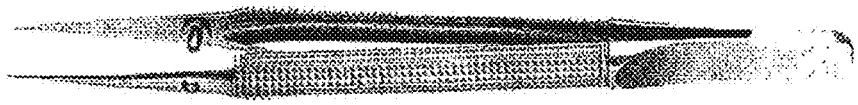
FIG. 11A illustrates an example of micro forceps for sewing provided with a lock mechanism for holding a sewing needle.
Figure 11B:
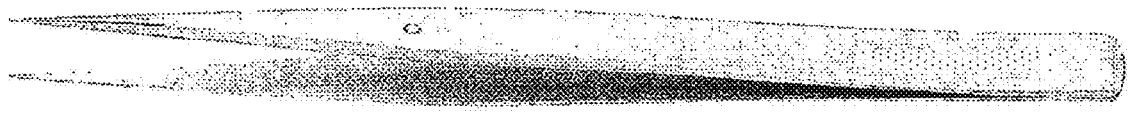
FIG. 11B illustrates an example of micro forceps not provided with a lock mechanism used for purposes other than sewing.
Figure 11C:
FIG. 11C illustrates an example of micro forceps for a deep portion used for an operation within the brain such as the pituitary gland.

FIGS. 11A to 11C are photographs that represent examples of tweezers as preferable gripping tools on which the plating process according to the embodiment of the present invention is performed.

FIG. 11A is an example of micro forceps for sewing provided with a lock mechanism intended to hold a sewing needle. FIG. 11B is an example of micro forceps not provided with a lock mechanism used for purposes other than sewing. FIG. 11C is an example of micro forceps for a deep portion used in an operation within the brain such as the pituitary gland or the like.

Gripping forces of the micro forceps illustrated in FIGS. 11A to 11C are improved by performing the plating process according to the embodiment of the present invention on the gripping surface on an inner side of the gripping part of the tip.

Effects of the tweezers in the embodiment are described below.

It can be anticipated that the tweezers such as the micro forceps or the like on which the plating process according to the embodiment of the present invention was performed can be gripped with a pinching force, applied to a gripped portion, of one-third to one-tenth of the pinching force of the tweezers of the comparison example in which the plating process was not performed on the gripping surface. Moreover, since the hardness of diamond grains in the tweezers on which the plating process according to the embodiment of the present invention was performed is high, it is superior in wear resistance.

Surfaces on which the plating process according to the embodiment of the present invention was performed are taken as examples and described below.

Figure 12A:
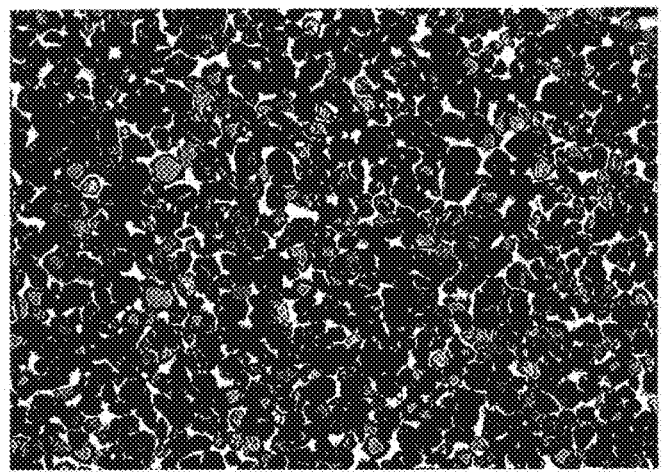
FIG. 12A is a photograph that represents one example of a surface on which the plating process according to the present invention was performed.
Figure 12B:
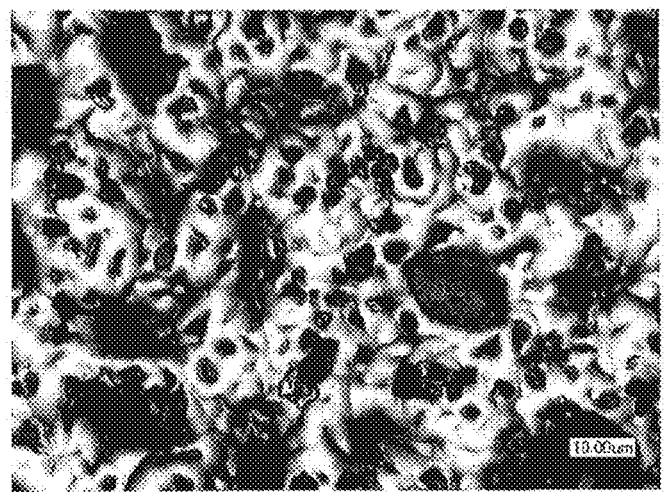
FIG. 12B is a photograph that represents another example of the surface on which the plating process according to the present invention was performed.
Figure 12C:
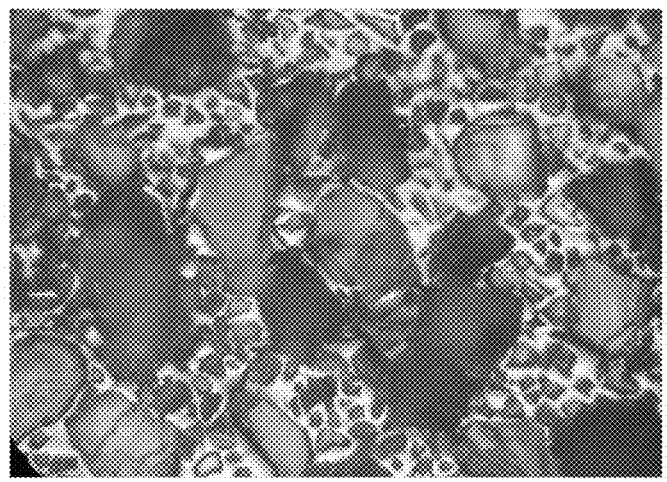
FIG. 12C is a photograph that represents a further example of the surface on which the plating process according to the present invention was performed.

FIGS. 12A to 12C are enlarged photographs that represent examples of the surfaces on which the plating process according to the embodiment of the present invention was performed.

Observing the surface of the enlarged photograph illustrated in FIG. 12A, diamond grains having a grain diameter of several μm are densely and evenly adhered. By performing the plating process with which diamond grains having a grain diameter of several μm are densely and evenly adhered, the gripping surface functions as a non-slip surface. By performing a plating process with which diamond grains having a grain diameter of several μm illustrated in FIG. 12A are densely and evenly adhered onto a nail of a conveyer that conveys a semiconductor product or the like, or a contact surface of a chuck, a roller or the like, the nail or the surface functions as a non-slip surface.

Additionally, observing the surface in the enlarged photograph illustrated in FIG. 12B, diamond grains having a grain diameter of several tens of μm are coarsely adhered, and those having a grain diameter of several μm are evenly adhered among the diamond grains having a grain diameter of several tens of μm. The height of the heads of the diamond grains having a grain diameter of several μm is lower than the height of the heads of the diamond grains having a grain diameter of several tens of μm. By implementing such a surface structure, spaces are created among the diamond grains having a grain diameter of several tens of μm. Therefore, a piece of flesh is pushed into the spaces among the diamond grains of a grain diameter of several 10 tens of μm when the piece of flesh is gripped. As a result, the griping force is improved. Plating with which diamond grains including those having grain diameters of two types illustrated in FIG. 12B are adhered is preferable as a plating process of a gripping surface of micro-tweezers (forceps) or the like that grips a biological membrane, a blood vessel, a piece of flesh or the like.

Furthermore, observing the surface of the enlarged photograph illustrated in FIG. 12C, diamond grains having a grain diameter of several tens of μm are adhered with a higher density than that in FIG. 12B, and diamond grains having a grain diameter of several μm are evenly adhered among the diamond grains having a grain diameter of several tens of μm. Thus, by implementing a structure where the diamond grains having a grain diameter of several tens of μm are adhered with high density, a gripping force can be increased even with a low pinching load. This is preferable as a plating process of a gripping surface of micro-tweezers (forceps or the like) that grips a biological membrane, a blood vessel, a piece of flesh or the like.

Modification examples of the embodiments according to the present invention are described last.

The embodiments according to the present invention have referred to examples where the plating processing method according to the present invention is applied to a needle holder for microsurgery, and micro forceps. However, the plating processing method according to the present invention is not limited to a needle holder for microsurgery, micro forceps and the like. The plating processing method according to the present invention is also applicable to other applications that serve a non-slip function implemented by a surface plating process, such as in assembly of a semiconductor, in disc brakes, in position alignment by a robot, or the like.

Additionally, the embodiments according to the present invention have referred to examples where the plating processing method according to the present invention is applied to a needle holder or micro forceps that an expert surgeon uses for microsurgery. However, the embodiments are also applicable to a gripping tool used in a medical robot, an endoscopic operation and a laparoscopic operation.

The embodiments according to the present invention have been described above. However, the present invention is not limited to the above described embodiments, and can be diversely configured or embodied within a scope that does not depart from the gist of the present invention.

What is claimed is:

1. A gripping tool, wherein
a plurality of first diamond grains having a first grain diameter which is a uniform size equal to or smaller than 140 μm are adhered onto a gripping surface by a first metal layer containing nickel in a thickness that does not exceed the first grain diameter in a state where the first diamond grains make contact with the gripping surface and are evenly distributed so that tops of the first diamond grains can be aligned, and
a plurality of second diamond grains having a second grain diameter smaller than the first grain diameter are adhered by a second metal layer, containing nickel, of the gripping surface onto the second metal layer containing nickel which is present on the first metal layer and in which the first diamond grains are not present, in a uniform thickness that causes heads of the diamond grains having the first grain diameter and the second grain diameter to protrude.

2. The gripping tool according to claim 1, further comprising
a gold-plated layer on surfaces of the second metal layer, and of the first and the second diamond grains adhered by the first and second metal layers.

3. The gripping tool according to claim 2 being a needle holder for gripping a sewing needle.

4. The gripping tool according to claim 2 being tweezers for an operation that grips a living tissue such as a biological membrane, a blood vessel or the like.

* * * * *

UNITED STATES PATENT AND TRADEMARK OFFICE
CERTIFICATE OF CORRECTION

Page 1 of 1

PATENT NO. : 10,883,186 B2
APPLICATION NO. : 15/905939
DATED : January 5, 2021
INVENTOR(S) : Takashi Konno It is certified that error appears in the above-identified patent and that said Letters Patent is hereby corrected as shown below:

On the Title Page

In item (73), in "Assignee", in Column 1, Line 1, delete "(CN)" and insert --(JP)-- therefor In the Claims In Column 15, Line 17, in Claim 1, delete "wherein" and insert --wherein:-- therefor In Column 16, Lines 12-13, in Claim 2, delete "comprising" and insert --comprising:-- therefor Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*